(12) United States Patent
Gertner

(10) Patent No.: US 10,843,012 B2
(45) Date of Patent: Nov. 24, 2020

(54) OPTIMIZED THERAPEUTIC ENERGY DELIVERY

(71) Applicant: Otsuka Medical Devices Co., Ltd., Tokyo (JP)

(72) Inventor: Michael Gertner, Menlo Park, CA (US)

(73) Assignee: Otsuka Medical Devices Co., Ltd., Tokyo (JP)

(*) Notice: Subject to any disclaimer, the term of this patent is extended or adjusted under 35 U.S.C. 154(b) by 1102 days.

(21) Appl. No.: 14/919,705

(22) Filed: Oct. 21, 2015

(65) Prior Publication Data

US 2016/0114194 A1 Apr. 28, 2016

Related U.S. Application Data

(60) Provisional application No. 62/122,493, filed on Oct. 22, 2014.

(51) Int. Cl.
| | |
|---|---|
| *A61N 7/00* | (2006.01) |
| *A61B 17/225* | (2006.01) |
| *A61B 8/13* | (2006.01) |
| *A61B 8/08* | (2006.01) |

(Continued)

(52) U.S. Cl.
CPC ............ *A61N 7/00* (2013.01); *A61B 17/2255* (2013.01); *A61B 17/2258* (2013.01); *A61B 8/00* (2013.01); *A61B 8/08* (2013.01); *A61B 8/13* (2013.01); *A61B 2090/378* (2016.02); *A61N 2007/0091* (2013.01)

(58) Field of Classification Search
CPC .............. A61N 7/00; A61N 2007/0091; A61B 17/2258; A61B 17/2255; A61B 8/00; A61B 8/08; A61B 8/13; A61B 2090/378
See application file for complete search history.

(56) References Cited

U.S. PATENT DOCUMENTS 5,048,527 A * 9/1991 Okazaki ............. A61B 17/2251
 600/439
5,394,875 A * 3/1995 Lewis ................. A61B 8/0833
 128/916

(Continued)

*Primary Examiner* — Peter Luong
(74) *Attorney, Agent, or Firm* — Eversheds Sutherland (US) LLP; Christopher C. Bolten; Sarah Waste

(57) ABSTRACT

An ultrasound apparatus is described for externally treating kidney stone in human body. The apparatus has one or more ultrasound imaging transducers, a therapeutic ultrasound transducer, and a processing unit. Optimized delivering of ultrasound energy to the kidney stone from the therapeutic ultrasound transducer is based on real-time tracked state (e.g., position, movement shape, size, or combination thereof) of the kidney stone. The ultrasound imaging transducer(s) is configured to image the stone during the application of the therapy treatment. An optimization algorithm is implemented to control the therapeutic ultrasound transducer to apply different force vectors to the region of the stone. The effect of the vectors in the differing directions with respect to the stone may be detected and input to the optimization algorithm, which optimizes the therapy by adjusting one or more of the vectors. Therefore, less ultrasound energy may be delivered to break the kidney stone, and may reduce the possibility of damaging the surrounding tissues of the kidney stone.

45 Claims, 13 Drawing Sheets

(51) Int. Cl.
*A61B 8/00* (2006.01)
*A61B 90/00* (2016.01)

(56) References Cited

U.S. PATENT DOCUMENTS

| | | | |
|---|---|---|---|
| 2004/0210214 A1* | 10/2004 | Knowlton | A61B 18/14 606/41 |
| 2006/0241525 A1* | 10/2006 | Lanski | A61B 17/22004 601/2 |
| 2007/0016113 A1* | 1/2007 | Buchholtz | A61B 17/2258 601/4 |
| 2011/0092781 A1* | 4/2011 | Gertner | A61B 5/055 600/301 |
| 2011/0257561 A1* | 10/2011 | Gertner | A61B 5/412 601/2 |
| 2015/0231414 A1* | 8/2015 | Ein-Gal | A61N 7/00 601/2 |

\* cited by examiner

OPTIMIZED THERAPEUTIC ENERGY DELIVERY

CROSS-REFERENCE TO RELATED APPLICATIONS

This application claims priority to and the benefit of U.S. Provisional Patent Application No. 62/122,493, filed on Oct. 22, 2014, the entire disclosure of the above application is expressly incorporated by reference herein.

INCORPORATION BY REFERENCE

The entireties of PCT application Nos. PCT/US10/52197 filed on Oct. 11, 2010, PCT/US10/52193 filed on Oct. 11, 2010, PCT/US13/57624 filed on Aug. 30, 2013, PCT/US14/22141 filed on Mar. 7, 2014, and PCT/US15/039258 filed on Jul. 6, 2015 are expressly incorporated by reference herein.

The entirety of U.S. Provisional Patent Application No. 62/075,487 filed on Nov. 5, 2014 is expressly incorporated by reference herein.

The entireties of the following U.S. Patent Applications are expressly incorporated by reference herein:

U.S. patent application Ser. No. 12/902,133 filed on Oct. 11, 2010

U.S. patent application Ser. No. 12/902,135 filed on Oct. 11, 2010

U.S. patent application Ser. No. 14/015,331 filed on Aug. 30, 2013

U.S. patent application Ser. No. 14/201,851 filed on Mar. 8, 2014

U.S. patent application Ser. No. 13/091,116 filed on Apr. 20, 2011

U.S. patent application Ser. No. 13/048,844 filed on Mar. 15, 2011

U.S. patent application Ser. No. 13/048,842 filed on Mar. 15, 2011

U.S. patent application Ser. No. 13/048,837 filed on Mar. 15, 2011

U.S. patent application Ser. No. 13/048,830 filed on Mar. 15, 2011

All publications and patent applications mentioned in this specification are herein incorporated by reference in their entirety, as if each individual publication or patent application was specifically and individually indicated to be incorporated by reference in its entirety.

TECHNICAL FIELD

An embodiment described herein relates generally to treatment of kidney stones.

BACKGROUND

Ultrasound technology is ubiquitous in modern medicine. Its most common uses in the past 20 years are mainly in the diagnostic imaging fields. However, in recent years, therapeutic uses of high intensity focused ultrasound in varying clinical applications have emerged. For example, the focused high intensity ultrasound can heat the tissue at the focal point, or the mechanical force generated from the ultrasound energy can gently nudge the tissue at the point to assess the stress and strain on the tissue. The focused ultrasound can also open up pores for delivery of molecules, genes, or drugs to the tissue. The focused ultrasound can move objects within the tissue as well and can vaporize tissue by the process of histotripsy.

Kidney stones are present in 10% of the US populations and are symptomatic in approximately half of these patients who are initially asymptomatic. Lithotripsy is a procedure in which shockwaves are delivered from a focused ultrasound transducer. The kidney stone is susceptible to the shockwave at the interface of the soft tissue and hard tissue of the stone which leads to breakage of the stone. The aiming of the lithotripsy therapy transducer is important to effective therapy. Obviously if the therapeutic wave misses the stone, the therapy will not be delivered at the correct dose or at the correct place. In lithotripsy, misfiring can result in damage to the kidney, more pain for the patient, and absence of treatment effect.

Improved systems for removing stones or breaking up stones are needed. For example, patent publication no. 20070016114 discusses a method whereby three dimensional CT scans are obtained for patients and these scans are utilized in current lithotripsy systems to aid in targeting stones for breakage and removal. In another example, U.S. Pat. No. 5,065,761 utilizes ultrasound imaging to assist in the process of relocating a stone after it has moved. In this way, minimal additional radiation is applied to the patient and the burdensome step of repositioning the patient after stone removal is simplified. Ultrasound is also contemplated in this patent for use in monitoring the progress of the treatment.

SUMMARY

A method of treating a kidney stone in a patient includes: placing an ultrasound imaging applicator at a first position that is external to the patient; placing a therapeutic ultrasound applicator at a second position that is external to the patient; imaging a kidney stone in a kidney of the patient with the ultrasound imaging applicator; determining a position of the kidney stone based on a result from the act of imaging; delivering energy from the therapeutic ultrasound transducer based on the determined position of the kidney stone; tracking a state that is associated with the kidney stone using the ultrasound imaging applicator; and operating the therapeutic ultrasound applicator based on the tracked state.

Optionally, the tracked state comprises a tracked position and/or a tracked orientation of the kidney stone.

Optionally, the therapeutic ultrasound applicator is operated to deliver additional energy based on the tracked position of the kidney stone.

Optionally, the tracked state comprises a movement of the kidney stone.

Optionally, the therapeutic ultrasound applicator is operated to deliver optimized ultrasound energy based on the tracked state.

Optionally, the tracked state comprises a shape and/or a size of the kidney stone.

Optionally, the therapeutic ultrasound applicator is operated to deliver additional energy if the kidney stone moves due to a previous energy delivery by the therapeutic ultrasound applicator.

Optionally, the method further includes determining whether to change a direction of energy delivery, a magnitude of the energy delivery, or both, by the therapeutic ultrasound applicator based on the tracked state.

Optionally, if the tracked state indicates that the kidney stone has moved due to the delivered energy, the therapeutic ultrasound applicator is operated to deliver additional energy having a same energy delivery direction as that of the delivered energy.

Optionally, if the tracked state indicates that the kidney stone has not moved or has not broken due to the delivered energy, the therapeutic ultrasound applicator is operated to deliver additional energy having a different energy delivery direction and/or a different energy level as that of the delivered energy.

Optionally, the delivered energy comprises a test dose.

Optionally, the therapeutic ultrasound applicator is configured to apply a series of energies to the kidney stone. The application of energies may be performed sequentially or simultaneously Optionally, the energies have different respective force vectors.

Optionally, the therapeutic ultrasound applicator comprises a set of ultrasound elements.

Optionally, the act of operating the therapeutic ultrasound applicator comprises electronically steering an aiming direction of the therapeutic ultrasound applicator.

Optionally, the method further includes determining a set of optimized ultrasound energy delivering parameters for one or more of the ultrasound elements.

Optionally, the method further includes determining a frequency, a pulse duration, a phase delay, a power level, or a combination of two or more of the foregoing, for one or more of the ultrasound elements.

Optionally, the method further includes providing optimized inputs for the therapeutic ultrasound applicator for different test positions.

Optionally, the method further includes providing semi-optimized inputs for the therapeutic ultrasound applicator for different test positions.

Optionally, the ultrasound imaging applicator and the therapeutic ultrasound applicator are integrated into a single component.

An apparatus for treating a kidney stone in a patient includes: an ultrasound imaging applicator for placement at a first position that is external to the patient, the ultrasound imaging applicator configured to image a kidney stone in a kidney of the patient; a therapeutic ultrasound applicator for placement at a second position that is external to the patient; and a processing unit configured to determine a position of the kidney stone based on an output from the ultrasound imaging applicator; wherein the therapeutic ultrasound applicator is configured to deliver energy based on the determined position of the kidney stone; and wherein the processing unit is configured to determine a state that is associated with the kidney stone after the energy is delivered, and operate the therapeutic ultrasound applicator based on the determined state.

Optionally, the determined state comprises a tracked position and/or a tracked orientation of the kidney stone.

Optionally, the therapeutic ultrasound applicator is configured to deliver additional energy based on the tracked position of the kidney stone.

Optionally, the determined state comprises a movement of the kidney stone.

Optionally, the therapeutic ultrasound applicator is configured to deliver additional energy if the kidney stone moves due to a previous energy delivery by the therapeutic ultrasound applicator.

Optionally, the determined state comprises a shape and/or a size of the kidney stone.

Optionally, the processing unit is configured to determine whether to change a direction of energy delivery, a magnitude of the energy delivery, or both, by the therapeutic ultrasound applicator based on the determined state.

Optionally, the therapeutic ultrasound applicator is configured to deliver additional energy having a same energy delivery direction as that of the delivered energy if the determined state indicates that the kidney stone has moved due to the delivered energy.

Optionally, the therapeutic ultrasound applicator is configured to deliver additional energy having a different energy delivery direction and/or a different energy level as that of the delivered energy if the determined state indicates that the kidney stone has not moved or has not broken due to the delivered energy.

Optionally, the delivered energy comprises a test dose.

Optionally, the delivered test dose may have very short duration and high magnitude. In some cases, multiple test doses are delivered in a short period of time, while imaging the stone for effect of one or more doses.

Optionally, the therapeutic ultrasound applicator is configured to apply a series of energies to the kidney stone.

Optionally, the energies have different respective force vectors.

Optionally, the therapeutic ultrasound applicator comprises a set of ultrasound elements forming a phased array.

Optionally, the apparatus further includes a mechanical mover configured to further move the phased array.

Optionally, the processing unit is configured to operate the therapeutic ultrasound applicator by electronically steering an aiming direction of the therapeutic ultrasound applicator.

Optionally, the processing unit is configured to determine a set of optimized energy delivering parameters for one or more of the ultrasound elements.

Optionally, the processing unit is configured to determine a frequency, a pulse duration, a phase delay, or a combination of two or more of the foregoing, for one or more of the ultrasound elements.

Optionally, the processing unit is configured to provide optimized inputs for the therapeutic ultrasound applicator for different test positions.

Optionally, the processing unit is configured to provide semi-optimized inputs for the therapeutic ultrasound applicator for different test positions.

Optionally, the ultrasound imaging applicator and the therapeutic ultrasound applicator are integrated into a single component.

Optionally, the apparatus further includes a 3D position tracking system to align the position of the kidney stone detected by the ultrasound imaging applicator with a position of an energy focus of the therapeutic ultrasound applicator.

Optionally, the therapeutic ultrasound applicator is configured to deliver the energy based also on a size and/or shape of the kidney stone.

Optionally, the therapeutic ultrasound applicator comprises a therapeutic transducer with a single ultrasound element.

Optionally, the apparatus further includes a mechanical mover configured to move the therapeutic transducer.

An apparatus to treat at least a portion of a kidney stone in a patient includes: an ultrasound imaging transducer configured to provide an image, wherein the ultrasound imaging transducer has fiducial markers coupled thereto to enable a feature in the image to be placed in a coordinate frame; a therapeutic ultrasound transducer configured to provide therapy to a region in the patient imaged by the ultrasound imaging transducer, wherein the therapeutic ultrasound transducer has fiducial markers coupled thereto to enable a position of the therapeutic ultrasound transducer to be placed in the coordinate frame; and a processing unit with a tracking algorithm configured to track a movement of a region of interest in the image created by the ultrasound imaging transducer; wherein the processing unit is configured to control the therapeutic ultrasound transducer to shift a focus, a direction, an intensity, or any combination of the foregoing, of energy delivery in response to the movement of the region of interest.

Optionally, the therapeutic ultrasound transducer is configured to apply a series of energies to the kidney stone.

Optionally, the energies have different respective force vectors.

Optionally, the therapeutic ultrasound transducer comprises a set of ultrasound elements.

Optionally, the processing unit is configured to determine a set of optimized energy delivering parameters for ultrasound elements of the therapeutic ultrasound transducer.

Optionally, the processing unit is configured to determine a frequency, a pulse duration, a phase delay, or a combination of two or more of the foregoing, for ultrasound elements of the therapeutic ultrasound transducer.

Optionally, the processing unit is configured to provide optimized inputs for the therapeutic ultrasound applicator for different test positions.

Optionally, the processing unit is configured to provide semi-optimized inputs for the therapeutic ultrasound applicator for different test positions.

Optionally, the processing unit is configured to operate the therapeutic ultrasound transducer to deliver a pulse of ultrasound energy to a region containing the kidney stone as a test dose to test for movement of the kidney stone.

Optionally, the processing unit comprises a programmable processor.

Optionally, the tracking algorithm is configured to also track a shape and/or size of the kidney stone.

Other features, embodiments, and advantageous will be described in the detailed description.

BRIEF DESCRIPTION OF THE DRAWINGS

FIG. 8 illustrates an example of some components in the device of FIG. 4.

DETAILED DESCRIPTION

Figure 1A:
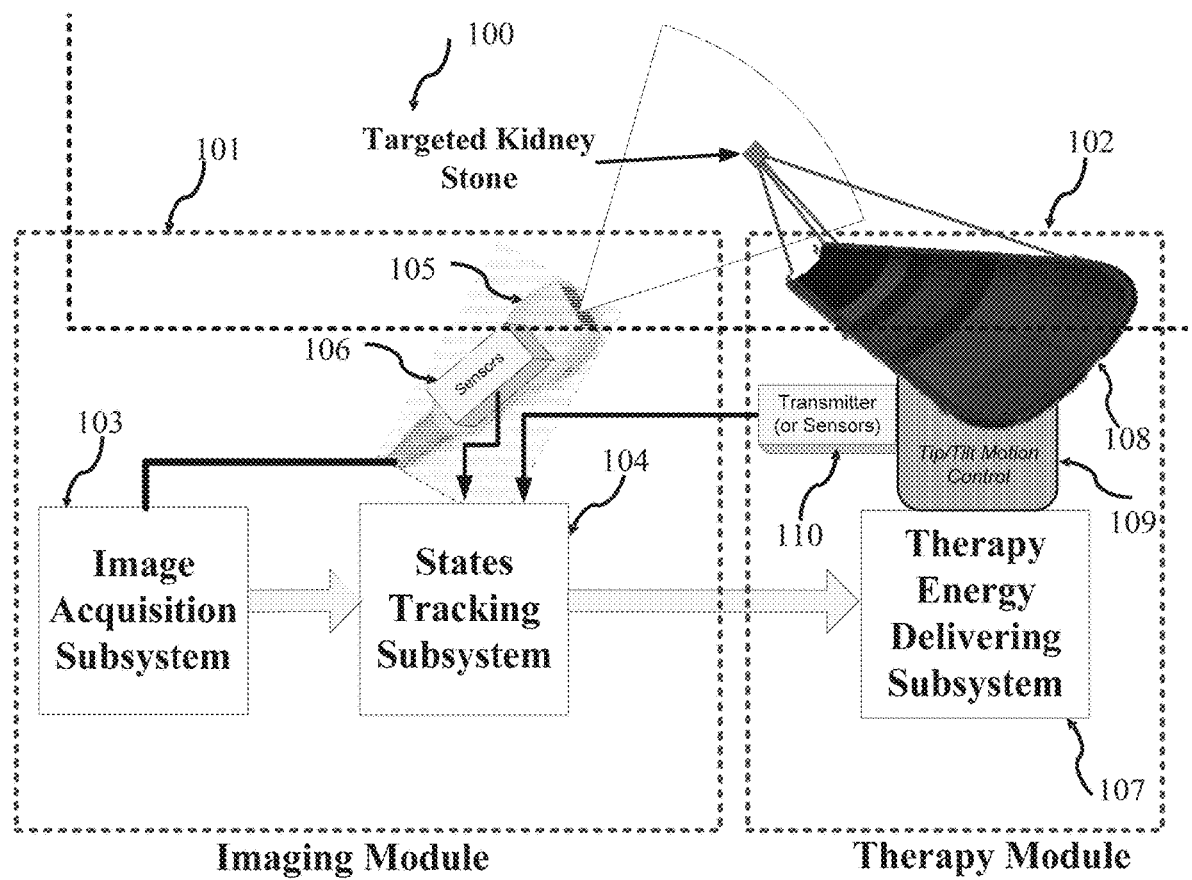
FIG. 1A illustrates a system for tracking, detecting and monitoring a region of an anatomical structure using ultrasound imaging and delivering therapy to push or break the targeted stone.

Various features are described hereinafter with reference to the figures. It should be noted that the figures may or may not be drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated or if not so explicitly described.

FIG. 1A illustrates a system 100 for tracking, detecting and monitoring a region of an anatomical structure using ultrasound imaging and delivering therapy to push or break the targeted stone, in accordance with some embodiments. As used in this specification, the term "anatomical structure" or any of other similar terms may refer to bodily tissue (such as organ tissue), or any structure inside a body (e.g., kidney stone), or both. As shown in FIG. 1A, the system 100 is configured for identifying at least one anatomical structure and tracking the position and motion of the anatomical structure using imaging before, during, and/or after delivery of a therapy to a patient. The system 100 includes an imaging module 101 and a therapy module 102. The imaging module 101 may be configured to acquire an image, identify one or more locations and/or features of an anatomical structure in the image, and/or track a location and/or movement of the anatomical structure within the image. The therapy module 102 of the system 100 may be configured to deliver therapy to a target stone.

The imaging module 101 may include an image acquisition subsystem 103 that functions to acquire an image. In some embodiments, the imaging module 101 may include a state tracking system 104 configured to track a location, movement and/or feature of an anatomical structure within the image acquired by the image acquisition subsystem 103. Thus, the state tracking system 104 may track one or more states that are associated with the anatomical structure. In some embodiments, the imaging module 101 may include an ultrasound imaging transducer 105 that transmits the ultrasound signals into the human body and receives the reflected signal from the tissue structures. In some embodiments, the imaging module 101 may further include position sensors 106 that are attached to the imaging transducer 105 to acquire the position of the imaging transducer 105 in 3D space and feed the position information to the state tracking subsystem 104. In some embodiments, the imaging transducer 105 may be linear, curved linear, phased, annular, or any of other types of imaging arrays that acquires an imaging plane inside a human body. In some embodiments, the imaging transducer 105 may be a two-dimensional array that acquires 3D ultrasound images inside a human body.

The therapy module 102 may include a therapy energy delivering subsystem 107, which is configured to generate controlled electrical energy to the ultrasound treatment transducer 108 that provides ultrasound energy into the targeted structure in a human body. In some embodiments, the ultrasound treatment transducer 108 may be a full circular annular phased array transmitting the focused ultrasound energy along an acoustic axis in depth direction into the targeted tissue structure in a human body. In other embodiments, the ultrasound treatment transducer 108 may be a section of full (e.g., partial) circular annular phased array configured to transmit the focused ultrasound energy along the acoustic axis in depth direction into the targeted tissue structure in a human body. In some embodiments, the therapy module 102 may include a tip/tilt motion control unit 109 that mechanically adjusts the ultrasound treatment transducer rotation in tip and tilt directions to follow the targeted tissue motion. In other embodiments, the control unit 109 may be configured to electronically control a phasing of transducer elements in the ultrasound treatment transducer to follow the targeted tissue motion. In further embodiments, the control of the ultrasound energy focus may be accomplished using both electronic phasing control of ultrasound elements in the ultrasound transducer 108 and mechanical control of the movement of the ultrasound transducer 108 by the therapy module 102. In some cases, such technique may allow control of ultrasound energy focus at any position within a huge treatment volume in 3D space. In some embodiments, the therapy module 102 may further include a transmitter and/or one or more position sensors of a 3D position system 110.

In some embodiments, the 3D position system determines the position of the ultrasound treatment transducer 108 and the relationship of the positions between the imaging transducer 105 and ultrasound treatment transducer 108. In some embodiments, an imaging ultrasound transducer 105 may be included near the therapy module 102, such that images may be acquired of the region of the anatomical structure being targeted, tracked, and treated, as will be described below.

As shown in FIG. 1A, in some embodiments, the state tracking subsystem 104 of imaging module 101 includes a tracker, a detector and a monitor. The tracker, detector and monitor are computer algorithms configured to identify and track a shape, location, movement and/or feature of a region of an anatomical structure in an image by searching within a region of interest in the image for a shape, location, movement and/or feature of the region of the anatomical structure. The tracker and detector may identify motion of an anatomical structure and compensate for the motion by adjusting the focal point and delivering direction, such that therapy may be delivered substantially continuously to a target region. In some embodiments, a monitor may use both a tracker and detector to identify and track micro air bubbles generated from the cavitation or partials of the broken stone in a region of an anatomical structure in an ultrasound image. The monitor feeds the states of the treatment on the target region to therapy energy delivering subsystem 107 and provides control signals for the adjusting of the intensity, direction, and/or position of the ultrasound energy delivery.

Figure 1B:
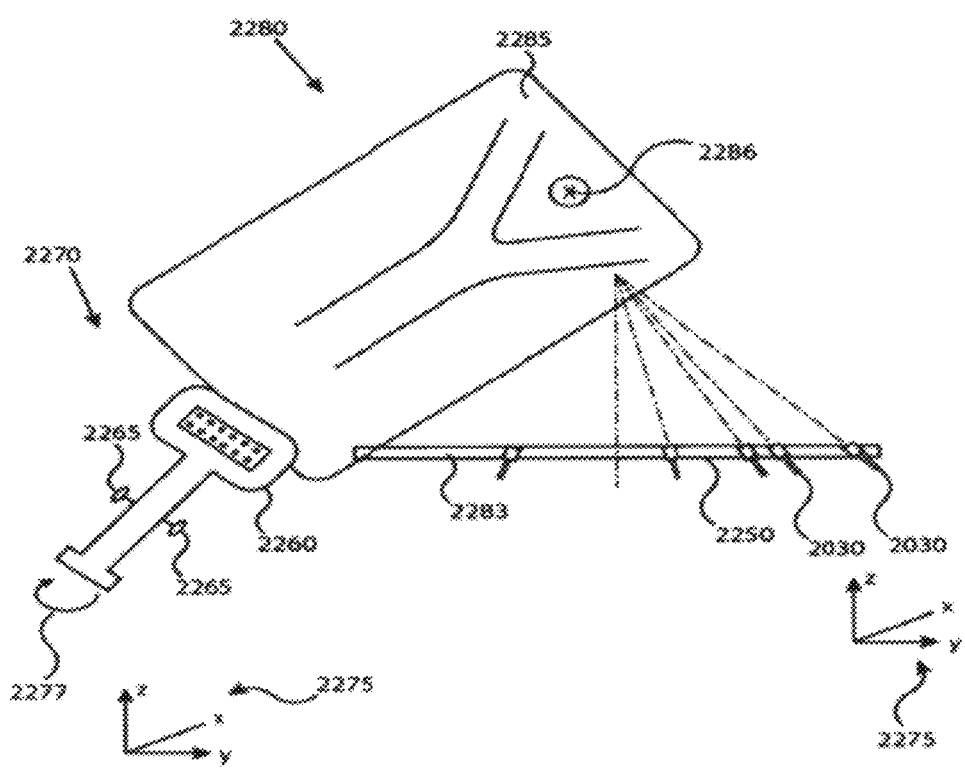
FIG. 1B illustrates an ultrasound imaging transducer and a therapy transducer being used in a method to treat kidney stone.

In FIG. 1B, a region of interest 2280 is shown being imaged by an ultrasound imaging transducer 2260. A stone in a location 2286 is imaged by the imaging transducer. Fiducials 2265 on the imaging transducer are calibrated to a coordinate reference frame 2275. This calibration enables the locating of the imaging transducer and all structures within the region of interest in the same coordinate reference frame 2275. Therapy transducer 2283 in one embodiment is a phased array therapy transducer with individual elements 2030 able to create a focus based on phase difference among the elements.

In one embodiment, the fiducials 2265 on the ultrasound imaging transducer are optical reflectors which can be visualized by a camera to create a coordinate reference 2275 for the transducer and by extension, a region in the human body being imaged by the transducer. The location of the therapy transducer is also determined by similar fiducials which can be imaged by a camera as well and correlated to the same coordinate reference frame 2275. The images from the camera (for example, of stone) serve to couple the imaging and therapy transducer together in a single coordinate reference frame 2275. A programmable interface is used to then deliver the proper phase signals to the individual elements 2030 on the platform containing the phased array. Proper phase signals refer to signals which link the ultrasound imaging and therapy transducers into the common reference frame 2275 so that the therapeutic ultrasound energy is delivered to the target 2286 identified by the imaging transducer 2260.

In one embodiment, the target 2286 is a kidney stone, or stone fragment if, after a stone breaking procedure the fragments do not pass into the ureter and excreted. The stone 2286 or stone region is targeted by the ultrasound imaging transducer 2260 and a region of interest (ROI) created around the stone region 2280. The ROI can be used to maintain the targeting of the stone during treatment. An ultrasound frame is obtained at least every 100 milliseconds (ms). In some embodiments, the frame is obtained every 50 ms or 25 ms or 1 ms. The region of interest in the frame is compared to the previous frame or set of previous frames for comparable features and to determine the degree of movement from the current frame to the previous frame. If movement has occurred, the position of the focus is adjusted to account for the movement. Tracking of the stone allows for the optimum safety and efficacy of the treatment of the stones.

Automated tracking of kidney stones and an ability to create varying foci with the array allow for an opportunity for a closed loop feedback program in which the stone is tracked with imaging and varying array force vectors are sent from the phased array transducer. The force vector which moves or breaks the stone(s), as determined by the imaging, will then become the preferred vector for that stone and optimizing treatment. The most modern equipment for kidney stones at the present time aims the shockwave (or pressure wave) in the direction of the stone based on fluoroscopic imaging and manual alignments without specific targeting and without the ability to follow or track the stone over time.

Figure 2:
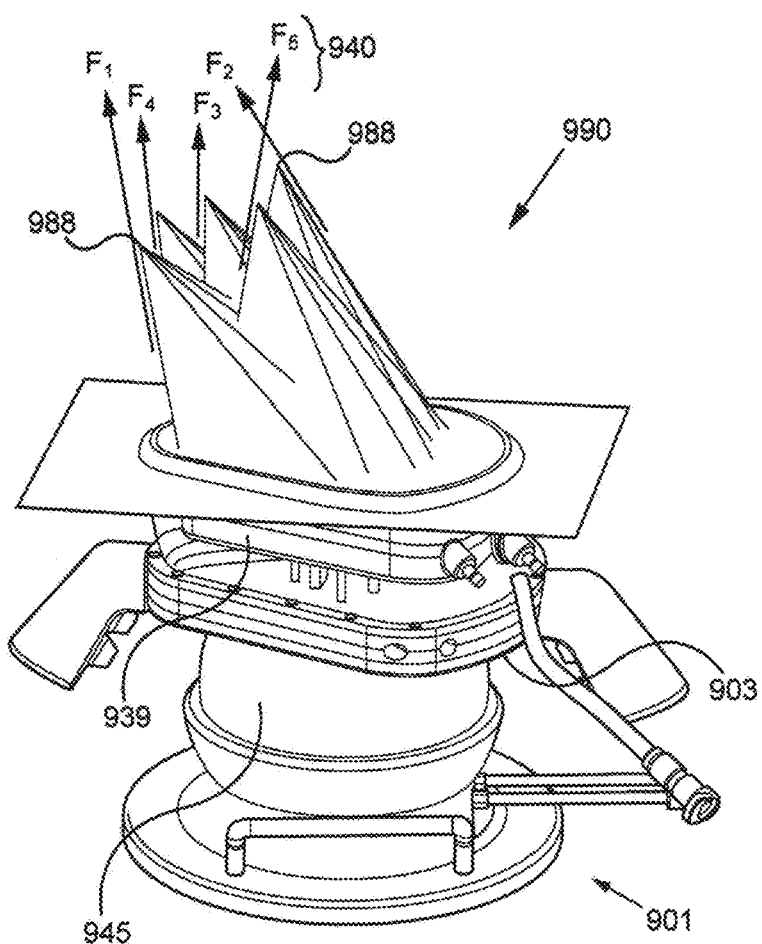
FIG. 2 illustrates an example of a therapeutic ultrasound applicator.

FIG. 2 depicts an example of a therapeutic ultrasound applicator 901 providing a set 990 of multiple focused ultrasound peaks 988. The force vectors F 940 corresponding to the peaks 988 are also shown. Platform 939 contains the therapeutic ultrasound transducer elements on a platform support. The transducer elements may be distributed on a spherical surface, an ellipsoid surface, or a surface of any other shape. The surface may be a flat surface or a non-flat surface, depending on the clinical requirements and transducer manufacturing process. The positions of the ultrasound peaks 988 can be chosen by a programmable processor which selects particular phases for the individual elements based on the planned position when a two dimensional therapeutic transducer is used. All the transducer elements can be utilized or only a subset of the elements of the phased array platform 939 can be used. The position of the ultrasound peaks 988 may be accomplished using a three dimensional mechanical motion of the transducer platform 939 with a single or multiple transducer elements, electronic phasing control, or a combination of mechanical motion of the transducer platform 939 and electronic phasing control of 1D or 2D therapeutic transducer elements. In the case where a single element is used, the number of peaks 988 separated spatially can be created by the mechanism of the motion control of the single element which can create the single peak. A single element cannot use phase controls to separate peaks. In such cases, positional control can only be accomplished by mechanical movement. Power and intensity can be modified and stone movement or breaking can be altered with these parameters as well in the case of the single element. The focused ultrasound peaks can be moved rapidly across the region of interest (various positions of peaks 988 in space) following the changes of the positions and/or orientations of the treatment target generated from the results of ultrasound system tracking, detecting and monitoring of the treatment target (e.g., based on kidney stone's position, orientation, movement, shape, size, or any combination of the foregoing). Also, force vectors with different directions may be generated based on the ultrasound peaks 988 during the treatment. The abilities to track, to detect and to monitor the states of the treatment target, or kidney stone and to apply varying directions and force vectors to a kidney stone are advantageous over previous technologies. These previous technologies cannot track the states and push or breakup kidney stone using varying and specific force vectors with differing and potentially optimized positions cannot be applied to the stones. The other system also cannot create forces in a closed loop system where the states of the target (e.g., position, movement, shape, etc.) and the effect of a force vector are assessed via imaging and then when there is a positive effect, a similar force vector is reapplied to the region. For example, previous systems as described in patent publication no EP 2560553 A2 can deliver focused ultrasound waves to the region of the stone to "push" a stone but do not automatically or specifically target the stone with the shockwave. It's also manually difficult to try each direction to push the stone even by an experienced operator. In some embodiments, the "pushing," or breaking is accomplished automatically which obviates the requirement for user feedback, patient re-positioning, etc. The operator or mechanical pusher simply applies the transducer to the skin of the patient, and the stone is identified by the operator or by a detection program. Then the system tracker and controller are allowed to take over and optimize the treatment of the stone. Once identified, the therapy can occur in an automated fashion, with the imager and tracker locked on to the target, and the controller and processors applying different test doses to the stone.

In some embodiments, mechanical motion of the treatment transducer may be accomplished using a mechanical mover. The mechanical mover may be configured to move the transducer by translating the transducer along a first direction (e.g., x-direction), translating the transducer along a second direction (e.g., y-direction that is perpendicular to the x-direction), translating the transducer along a third direction (e.g., z-direction that is perpendicular to the x and y directions), tilting about a first axis (e.g., x-axis), tilting about a second axis (e.g., y-axis that is perpendicular to the x-axis), tilting about a third axis (e.g., z-axis that is perpendicular to the x and y axes), or any combination of two or more of the foregoing.

Figures 5A, 5B, 5C, 5D, 5E:
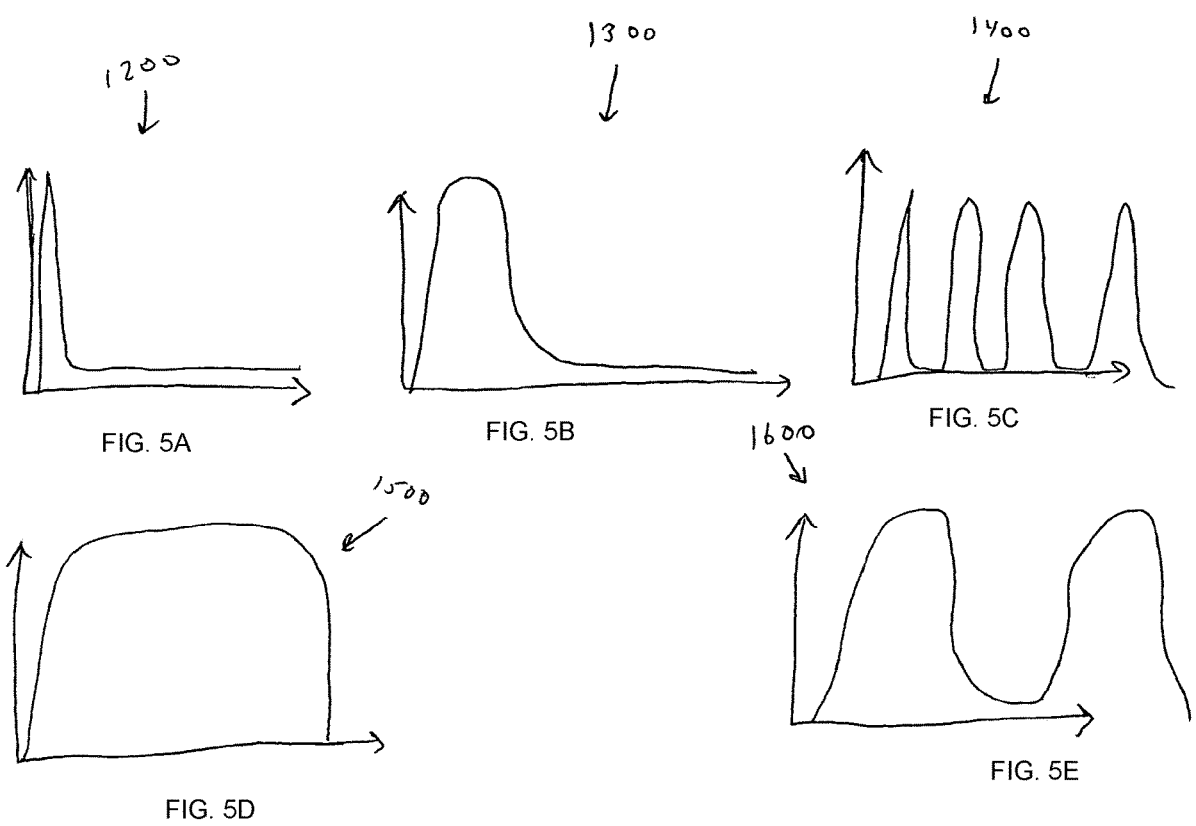
FIGS. 5A-5E illustrate examples of burst(s) that may be applied using a therapeutic ultrasound applicator.

In addition to phased array, a mechanical mover 939 can also be incorporated into the therapeutic ultrasound transducer to further enhance the ability to move the foci emanating from the array. For example, the elements of the phased array can move the focus in a 1 cm cubic region through electronic focusing and then the mechanical movement can augment the movement in a 3 cm×3 cm cube to further augment the position range of the focus. The mechanical mover of the transducer 939 can augment the phase control movement of the ultrasound energy, creating a large range of potential treatment positions and delivering directions for the focus of ultrasound energy. For example, a vector is a combination of force and direction. With focused ultrasound, "force" in fact comprises many variables. For example, force can be repetitive in short bursts with defined time between bursts and with high amplitude or the bursts can be long and constant. Examples of different amplitudes and bursts are shown in FIG. 5. FIG. 5A is a brief high amplitude burst (1 ms) with a frequency from 100 kHz to 4 MHz, and more preferably from 250 kHz to 1 MHz. FIG. 5B is a burst with a slightly longer decay but also can have a frequency from 100 kHz to 4 MHz, and more preferably from 250 kHz to 1 MHz. FIG. 5C shows a quick start and stop with respect to bursts from the therapy array. FIG. 5D represents a longer burst which might be as long as 100 ms or as short as 5 ms. The vector of the approaching wave may vary in the three dimensions in any of these depictions. In other words, even though the shockwaves appear on two dimensional X-Y graphs, a third dimension (Z direction) can be add to the movement as well.

Figure 3:
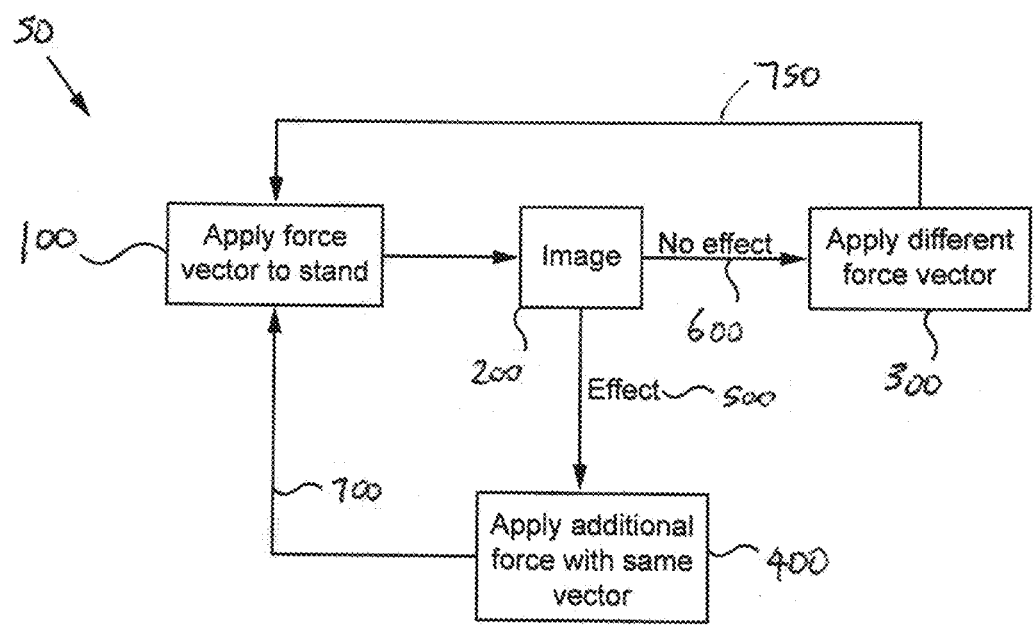
FIG. 3 illustrates a method of treating kidney stone.

A method of treating kidney stone is shown in FIG. 3. The method involves a "Closed loop" 50. In this example, a force vector is applied to the region of interest (item 100) while the region is being imaged (item 200). Typically, the region has a tissue structure of interest (e.g. a kidney stone). If there is positive effect 500 in the image related to the stone (e.g. movement, breaking, patient sensation, etc), the same, or similar, force vector can be applied again (item 400). If no effect (item 600) is seen in the reimaging, then a different force vector is applied (item 300). The application of force vector is then repeated (loop arrow 750). If the force vector was successful, then the identical force vector is continued (item 400). In the ensuing force vector application, the successful force vector may be repeated (loop arrow 700) and another vector might be applied immediately to continue to test as far as the effect on the stone in case with stone movement, the optimal direction of force changes.

The programmable processor can be programmed or configured to send random inputs or semi-random inputs to the phaseable elements in different test positions. For example, while imaging a region with a kidney stone, a random or a focus with a unique or strategic force vectors can be assessed for its effect on movement of a stone. If one focal position elicits movement of the stone, then that angle or region might be further utilized in stone movement or breaking. This is a path of least resistance strategy. If a focal direction moves the stone or breaking is indicated, then that focal direction is continued by the processor. The focal path with the most optimum force direction to effect therapy is further utilized to continue to push or break the stone. The random inputs can vary angle, position in x-y-z coordinate reference, average intensity, peak intensity, pulse width, duty cycle, and decay from duty cycle. The tracking algorithm is configured to localize a selected region and follow it with time. This region can include a stone or stone fragment. The region being tracked and the focal direction being tracked is then the region in which focused ultrasound is applied so as to fragment or move the stone.

Figure 4:
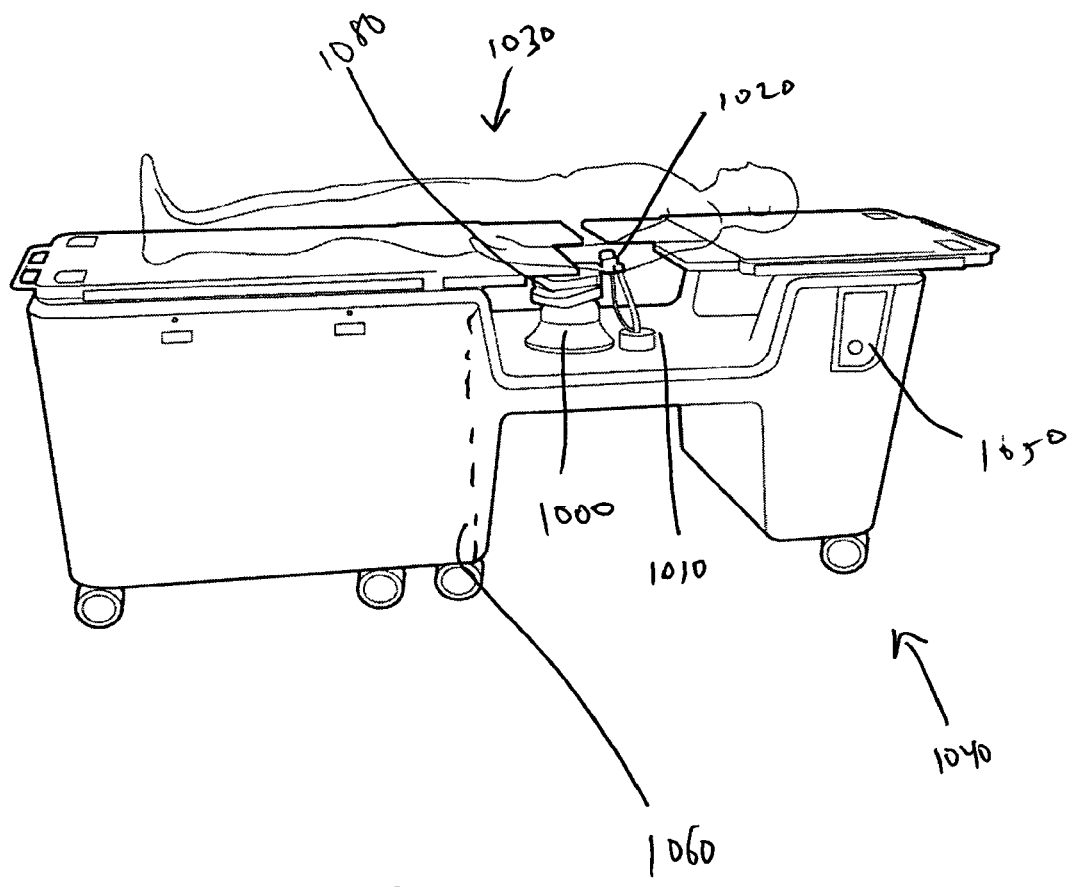
FIG. 4 illustrates a device with a patient support and a therapeutic ultrasound transducer for treating kidney stone.

FIG. 4 depicts a complete integrated system to treat kidney stones. An imaging unit 1010 and a therapy unit 1000 are provided. In some embodiments they are mechanically coupled and in other preferred embodiments, they are not mechanically coupled but are coupled in space through sensors such as optical sensors. A key improvement in the treatment of kidney stones accordance to one or more embodiments described herein is the ability to localize the stone with imaging and then directly target the stone region with a focused ultrasound wave. The configuration shown in FIG. 4, where the imaging and therapy modules are separated, allows for maximal flexibility to remove the stone from the kidney. With therapy and imaging uncoupled, stones can be imaged from an optimal direction and treated independently in an optimal direction for therapy. The coupling between the imaging and therapy is accomplished by optical imaging fiducials in one example. These fiducials and associated lighting allow the imaging and therapy transducers to sit in the same coordinate frame. The integrated table enables fast and convenient set up in almost any setting. The ultrasound imaging is utilized to locate the stone and because it is not coupled to the therapy transducer can be placed in an optimal position for imaging.

As discussed, one or more embodiments described herein involve use of an ultrasound array to deliver a sequence of energies to treat (e.g., to move, to break up, or both) kidney stone. In some embodiments, the array may be a phased array that provides fine resolution to effect the movement and/or breakage of the kidney stone. During use, the effect of treatment energy on the kidney stone is monitored (e.g., using imaging). If there is movement and/or breakage of the kidney stone, then additional energy is delivered based on the detected movement and/or breakage of the kidney stone. In some cases, the direction and energy parameter(s) for the additional energy may be maintained to be the same as those for the previous energy that caused the movement and/or breakage. In other cases, the direction and/or the energy parameter(s) for the additional energy may be adjusted to be different from those for the previous energy that caused the movement and/or breakage. For example, if the previous energy resulted in a breakage of the kidney stone, then the next energy may be delivered at the same angle to the same location, but using a higher intensity, in order to attempt to further break up the kidney stone. As another example, if the previous energy resulted in a movement of the kidney stone, then the next energy may be delivered at a slightly different location, using the same or different intensity, in order to further move the kidney stone. The different location may be, for example, less than 3 mm, less than 2 mm, less than 1 mm, less than 0.5 mm, or at other distances, from the last location (e.g., the last position of the energy focus). Also, in some cases, multiple energies may be delivered back and forth at two or more different locations in order to rock the stone back and forth and loosed it from its surrounding tissue. The process continues to result in a series of energies being delivered to treat the kidney stone. For example, the apparatus described herein may be configured to provide different phase directions and powers, one after the other, while movement or effect on the stone from the energy delivery is being monitored (e.g., using images from the imaging device).

Detail features of the imaging unit 1010 and the therapy unit 1000 are illustrated in FIGS. 7-12.

Figure 6:
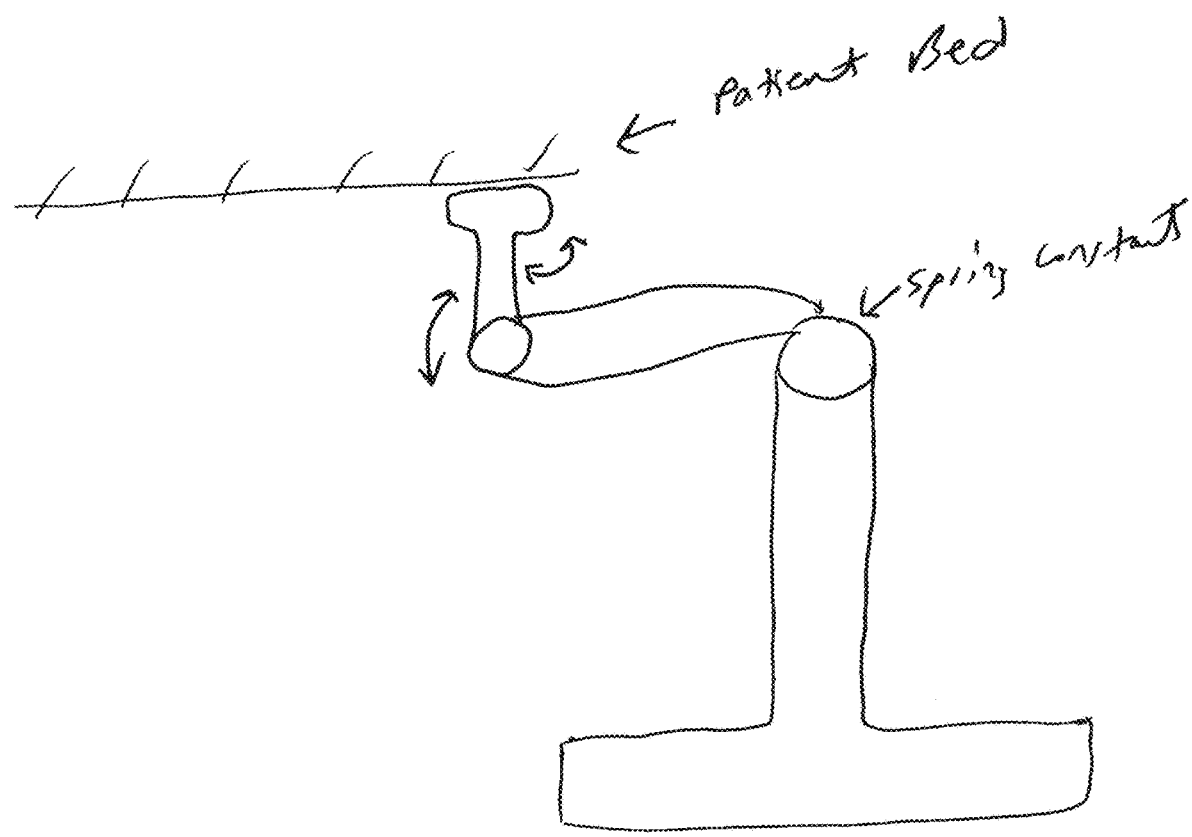
FIG. 6 illustrates an example of an arm for an imaging probe.
Figure 7:
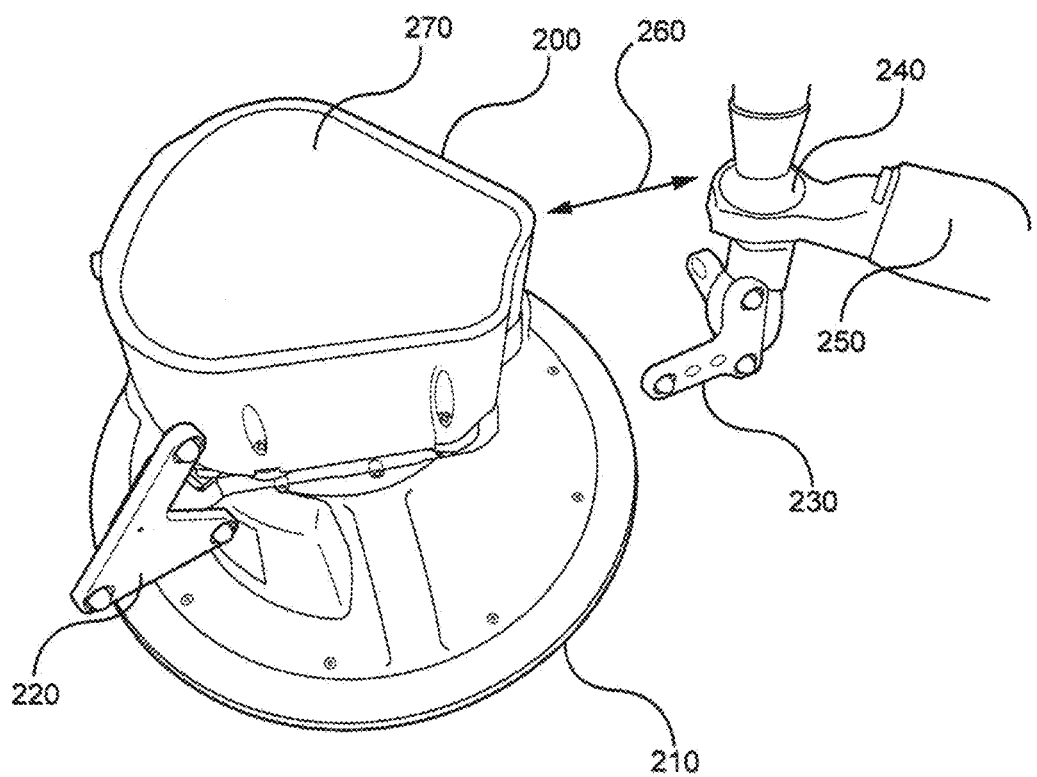
FIG. 7 illustrates an example of some components in the device of FIG. 4.
Figure 7:
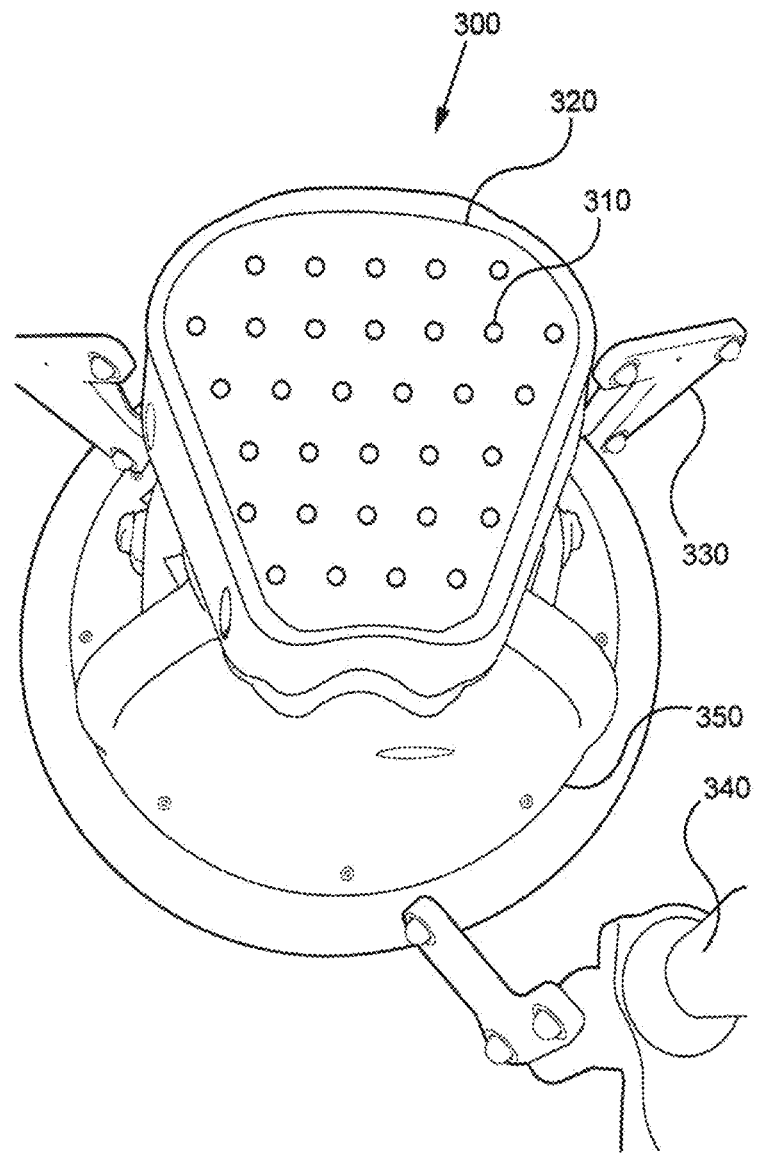
Figure 9:
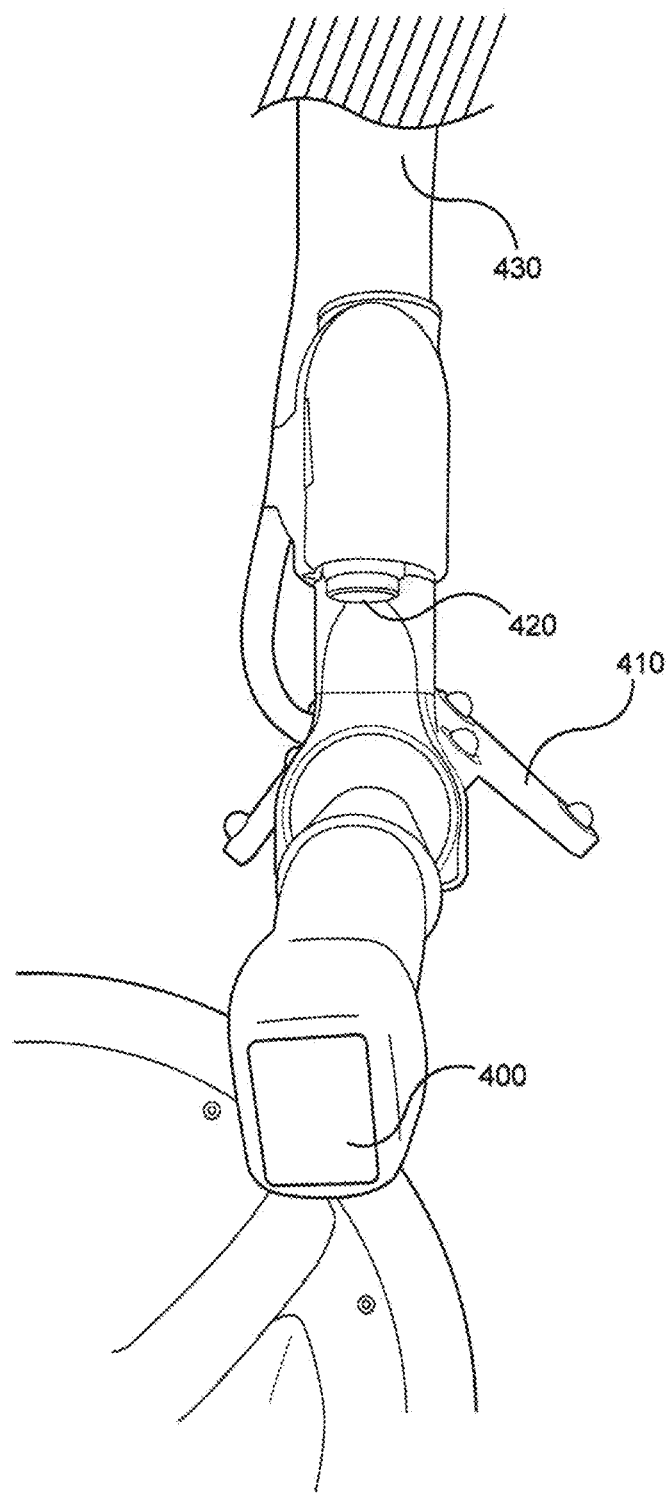
FIG. 9 illustrates an example of some components in the device of FIG. 4.
Figure 10:
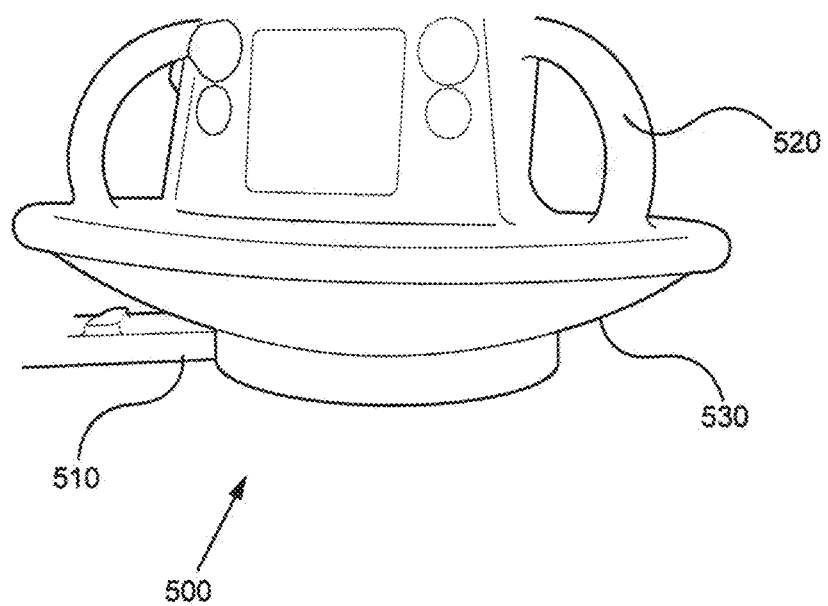
FIG. 10 illustrates an example of some components in the device of FIG. 4.
Figure 11:
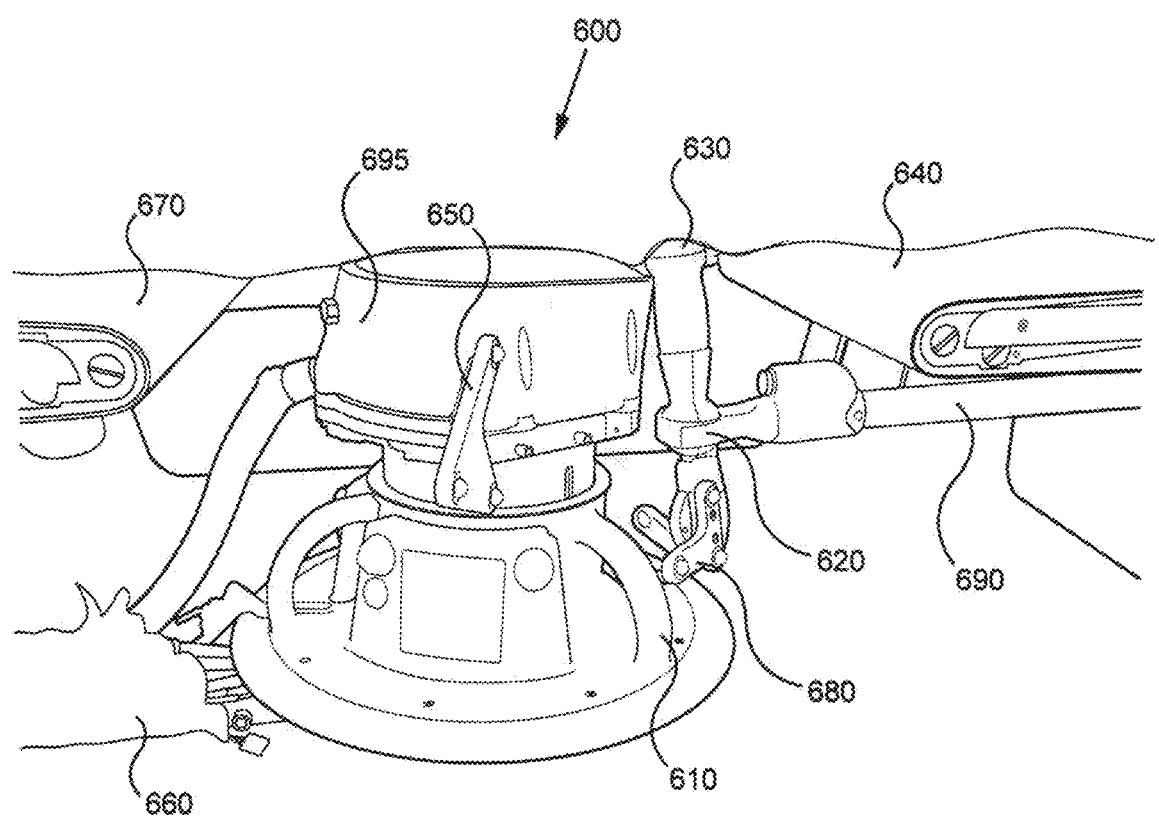
FIG. 11 illustrates an example of some components in the device of FIG. 4.
Figure 12:
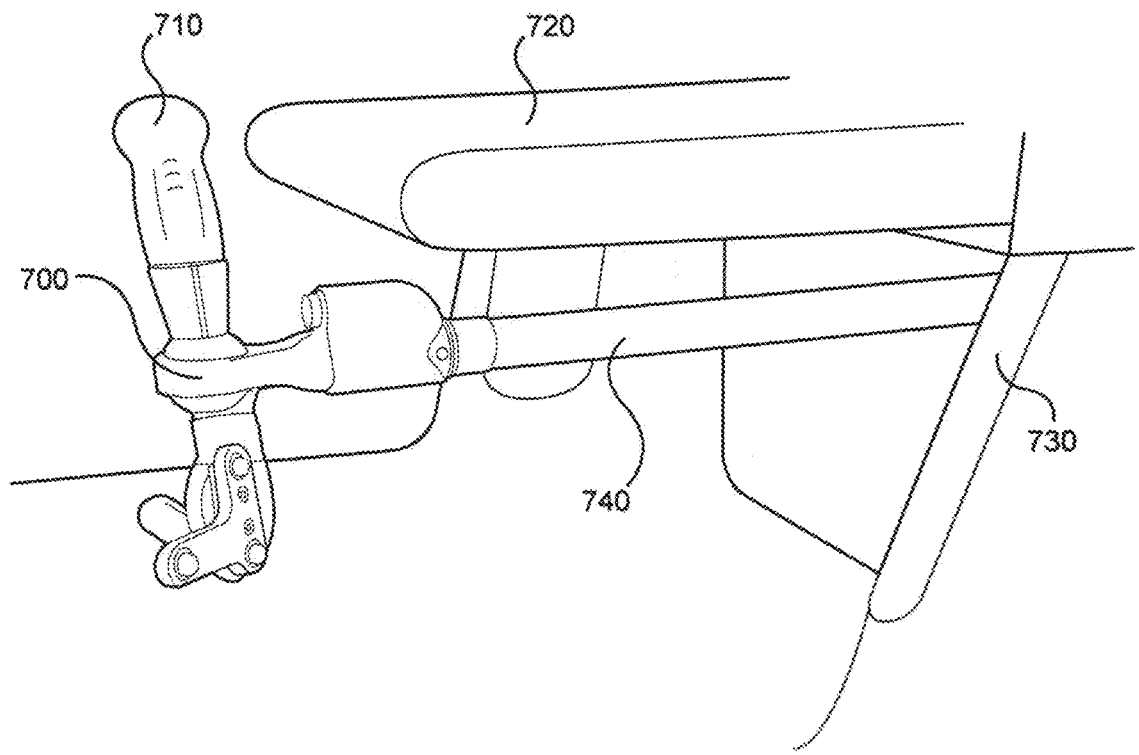
FIG. 12 illustrates an example of some components in the device of FIG. 4.

FIG. 6 depicts a close up of an arm on the imaging probe which allows for locking of the probe in an optimal position underneath the patient. Optical fiducials are placed strategically on the imaging arm and the therapeutic transducer so that each knows where the other is and any point in the image can be targeted by the therapy transducer.

The therapy transducer, likewise, has 6 degrees of freedom for placement relative to the imaging transducer as well as optical fiducials strategically placed on its exterior. Furthermore, the therapy transducer in one preferred embodiment is a phased array transducer with multiple elements, each of which is independently controllable by a programmable processor. The therapeutic array might have 2, 10, 100, 1000, 10,000 independently controllable elements each of which can be couple to the imaging information to identify an optimal strategy for removal of the stone. As described above, the optimal strategy might involve a specific focal vector, a set of elements to create an alternative focal vector, a specific phasing program of ultrasound frequency, phase pattern, burst on-off time, peak power, etc to optimize the removal of the stone.

In some cases, the apparatus described herein is configured for delivering optimized minimum ultrasound energy to the kidney stone, thereby reducing the possibility of damaging the surrounding tissues of the kidney stone In the above embodiments, the apparatus and method have been described with reference to having one imaging applicator. In other embodiments, the apparatus may include multiple imaging applicators (e.g., multiple ultrasound imaging applicators) placed at different locations external to the patient. Such apparatus allows imaging of the target region from different angles to obtain images at different imaging planes.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

What is claimed is:

1. A method of treating a kidney stone in a patient comprising:
    placing an ultrasound imaging applicator at a first position that is external to the patient;
    placing a therapeutic ultrasound applicator at a second position that is external to the patient;
    imaging a kidney stone in a kidney of the patient with the ultrasound imaging applicator;
    determining a position of the kidney stone based on a result from the act of imaging;
    delivering energy from the therapeutic ultrasound transducer based on the determined position of the kidney stone;
    tracking a state that is associated with the kidney stone using the ultrasound imaging applicator; and
    operating the therapeutic ultrasound applicator based on the tracked state;
    wherein the method further comprises determining whether to change a direction of energy delivery by the therapeutic ultrasound applicator based on the tracked state; and
    wherein if the tracked state indicates that the kidney stone has moved due to the delivered energy, the therapeutic ultrasound applicator is operated to deliver additional energy having a same energy delivery direction as that of the delivered energy.

2. The method of claim 1, wherein the tracked state comprises a tracked position and/or a tracked orientation of the kidney stone.

3. The method of claim 2, wherein the therapeutic ultrasound applicator is operated to deliver additional energy based on the tracked position of the kidney stone.

4. The method of claim 1, wherein the tracked state comprises a movement of the kidney stone.

5. The method of claim 1, wherein the therapeutic ultrasound applicator is operated to deliver additional energy having the same energy delivery direction if the kidney stone breaks due to a previous energy delivery by the therapeutic ultrasound applicator.

6. The method of claim 1, wherein the tracked state comprises a shape and/or a size of the kidney stone.

7. The method of claim 1, wherein the therapeutic ultrasound applicator is operated to deliver additional energy having an intensity that is the same as that of the delivered energy if the kidney stone moves due to a previous energy delivery by the therapeutic ultrasound applicator.

8. The method of claim 1, wherein the delivered energy comprises a test dose.

9. The method of claim 1, wherein the therapeutic ultrasound applicator is configured to apply a series of energies to the kidney stone.

10. The method of claim 9, wherein the energies have different respective force vectors.

11. The method of claim 1, wherein the therapeutic ultrasound applicator comprises a set of ultrasound elements.

12. The method of claim 11, wherein the act of operating the therapeutic ultrasound applicator comprises electronically steering an aiming direction of the therapeutic ultrasound applicator.

13. The method of claim 11, further comprising determining a set of energy delivering parameters for one or more of the ultrasound elements.

14. The method of claim 11, further comprising determining a frequency, a pulse duration, a phase delay, a power level, or a combination of two or more of the foregoing, for one or more of the ultrasound elements.

15. The method of claim 1, further comprising providing inputs for the therapeutic ultrasound applicator to deliver test doses for different respective test positions.

16. The method of claim 1, wherein the ultrasound imaging applicator and the therapeutic ultrasound applicator are integrated into a single component.

17. An apparatus for treating a kidney stone in a patient comprising:
an ultrasound imaging applicator for placement at a first position that is external to the patient, the ultrasound imaging applicator configured to image a kidney stone in a kidney of the patient;
a therapeutic ultrasound applicator for placement at a second position that is external to the patient; and
a processing unit configured to determine a position of the kidney stone based on an output from the ultrasound imaging applicator;
wherein the therapeutic ultrasound applicator is configured to deliver energy based on the determined position of the kidney stone;
wherein the processing unit is configured to determine a state that is associated with the kidney stone after the energy is delivered, and operate the therapeutic ultrasound applicator based on the determined state;
wherein the processing unit is configured to determine whether to change a direction of energy delivery by the therapeutic ultrasound applicator based on the determined state; and
wherein if the state indicates that the kidney stone has moved due to the delivered energy, the therapeutic ultrasound applicator is configured to deliver additional energy having a same energy delivery direction as that of the delivered energy.

18. The apparatus of claim 17, wherein the determined state comprises a tracked position and/or a tracked orientation of the kidney stone.

19. The apparatus of claim 17, wherein the additional energy has a different energy level as that of the delivered energy.

20. The apparatus of claim 17, wherein the determined state comprises a movement of the kidney stone.

21. The apparatus of claim 17, wherein the determined state comprises a shape and/or a size of the kidney stone.

22. The apparatus of claim 17, wherein the delivered energy comprises a test dose.

23. The apparatus of claim 17, wherein the therapeutic ultrasound applicator is configured to apply a series of energies to the kidney stone.

24. The apparatus of claim 23, wherein the energies have different respective force vectors.

25. The apparatus of claim 17, wherein the therapeutic ultrasound applicator comprises a set of ultrasound elements forming a phased array.

26. The apparatus of claim 25, wherein the processing unit is configured to operate the therapeutic ultrasound applicator by electronically steering an aiming direction of the therapeutic ultrasound applicator.

27. The apparatus of claim 25, wherein the processing unit is configured to determine a set of energy delivering parameters for one or more of the ultrasound elements.

28. The apparatus of claim 25, wherein the processing unit is configured to determine a frequency, a pulse duration, a phase delay, or a combination of two or more of the foregoing, for one or more of the ultrasound elements.

29. The apparatus of claim 25, further comprising a mechanical mover configured to further move the phased array.

30. The apparatus of claim 17, wherein the processing unit is configured to provide inputs for the therapeutic ultrasound applicator for different test positions.

31. The apparatus of claim 17, wherein the ultrasound imaging applicator and the therapeutic ultrasound applicator are integrated into a single component.

32. The apparatus of claim 17, further comprising a 3D position tracking system to align the position of the kidney stone detected by the ultrasound imaging applicator with a position of an energy focus of the therapeutic ultrasound applicator.

33. The apparatus of claim 17, wherein the therapeutic ultrasound applicator is configured to deliver the energy based also on a size and/or shape of the kidney stone.

34. The apparatus of claim 17, wherein the therapeutic ultrasound applicator comprises a therapeutic transducer with a single ultrasound element.

35. The apparatus of claim 34, further comprising a mechanical mover configured to move the therapeutic transducer.

36. An apparatus to treat at least a portion of a kidney stone in a patient comprising:
an ultrasound imaging transducer configured to provide an image, wherein the ultrasound imaging transducer has fiducial markers coupled thereto to enable a feature in the image to be placed in a coordinate frame;
a therapeutic ultrasound transducer configured to provide therapy to a region in the patient imaged by the ultrasound imaging transducer, wherein the therapeutic ultrasound transducer has fiducial markers coupled thereto to enable a position of the therapeutic ultrasound transducer to be placed in the coordinate frame; and a processing unit with a tracking algorithm configured to track a movement of a region of interest in the image created by the ultrasound imaging transducer;

wherein the processing unit is configured to control the therapeutic ultrasound transducer to shift a focus, a direction, an intensity, or any combination of the foregoing, of energy delivery in response to the movement of the region of interest; and wherein the therapeutic ultrasound applicator is configured to deliver additional energy having a same energy delivery direction as that of the delivered energy if a state of the kidney stone indicates that the kidney stone has moved.

37. The apparatus of claim 36, wherein the therapeutic ultrasound transducer is configured to apply a series of energies to the kidney stone.

38. The apparatus of claim 37, wherein the energies have different respective force vectors.

39. The apparatus of claim 38, wherein the therapeutic ultrasound transducer comprises a set of ultrasound elements.

40. The apparatus of claim 39, wherein the processing unit is configured to determine a set of energy delivering parameters for ultrasound elements of the therapeutic ultrasound transducer.

41. The apparatus of claim 39, wherein the processing unit is configured to determine a frequency, a pulse duration, a phase delay, or a combination of two or more of the foregoing, for ultrasound elements of the therapeutic ultrasound transducer.

42. The apparatus of claim 36, wherein the processing unit is configured to provide inputs for the therapeutic ultrasound applicator for different test positions.

43. The apparatus of claim 36, wherein the processing unit is configured to operate the therapeutic ultrasound transducer to deliver a pulse of ultrasound energy to a region containing the kidney stone as a test dose to test for movement of the kidney stone.

44. The apparatus of claim 36, wherein the processing unit comprises a programmable processor.

45. The apparatus of claim 36, wherein the tracking algorithm is configured to also track a shape and/or size of the kidney stone.

* * * * *